(12) United States Patent
Yanagisawa et al.

(10) Patent No.: US 10,131,646 B2
(45) Date of Patent: Nov. 20, 2018

(54) AROMATIC SULFONIUM SALT COMPOUND, PHOTOACID GENERATOR, RESIST COMPOSITION, CATIONIC POLYMERIZATION INITIATOR, AND CATIONICALLY POLYMERIZABLE COMPOSITION

(71) Applicant: ADEKA CORPORATION, Tokyo (JP)

(72) Inventors: Satoshi Yanagisawa, Tokyo (JP); Hitomi Toda, Tokyo (JP); Koichi Shigeno, Tokyo (JP); Masaki Kimura, Tokyo (JP)

(73) Assignee: ADEKA CORPORATION, Tokyo (JP)

( * ) Notice: Subject to any disclaimer, the term of this patent is extended or adjusted under 35 U.S.C. 154(b) by 0 days.

(21) Appl. No.: 15/558,830

(22) PCT Filed: Mar. 18, 2015

(86) PCT No.: PCT/JP2015/058119
§ 371 (c)(1),
(2) Date: Sep. 15, 2017

(87) PCT Pub. No.: WO2016/147356
PCT Pub. Date: Sep. 22, 2016

(65) Prior Publication Data
US 2018/0079738 A1 Mar. 22, 2018

(51) Int. Cl.
| | | |
|---|---|---|
| *C07D 311/16* | (2006.01) | |
| *C07C 309/30* | (2006.01) | |
| *C07C 309/06* | (2006.01) | |
| *G03F 7/004* | (2006.01) | |
| *C08G 59/68* | (2006.01) | |

(52) U.S. Cl.
CPC .......... *C07D 311/16* (2013.01); *C07C 309/06* (2013.01); *C07C 309/30* (2013.01); *C08G 59/687* (2013.01); *G03F 7/0045* (2013.01)

(58) Field of Classification Search
CPC ... C07D 311/16; C07C 309/06; C07C 309/30; C08G 59/687; C08G 59/68; G03F 7/0045; G03F 7/004
USPC ......................................................... 549/285
See application file for complete search history.

(56) References Cited

U.S. PATENT DOCUMENTS

| | | |
|---|---|---|
| 6,162,881 A | 12/2000 | Schön et al. |
| 2005/0233253 A1 | 10/2005 | Ishihara et al. |
| 2012/0130117 A1 | 5/2012 | Makabe et al. |
| 2012/0136155 A1 | 5/2012 | Makabe et al. |
| 2013/0143159 A1 | 6/2013 | Iwashita et al. |
| 2016/0077440 A1 | 3/2016 | Yamanaka et al. |

FOREIGN PATENT DOCUMENTS

| | | |
|---|---|---|
| JP | 09-52891 A | 2/1997 |
| JP | 11-35613 A | 2/1999 |
| JP | 2002-293816 A | 10/2002 |
| JP | 2011-105645 A | 6/2011 |
| JP | 2012-248583 A | 12/2012 |

(Continued)

OTHER PUBLICATIONS

Unverified Machine Translation of Japanese patent application, JP 2014094925, Proquest; published May 22, 2014. (Year: 2014).*
Unverified Machine Translation of Japanese patent application, JP JP2002293816, Proquest; published Oct. 9, 2002. (Year: 2002).*
International Search Report for PCT/JP2015/058119 (PCT/ISA/210) dated May 19, 2015.
Office Action for Japanese Application No. 2014-042166 dated Sep. 12, 2017.

(Continued)

*Primary Examiner* — Daniel R Carcanague
(74) *Attorney, Agent, or Firm* — Birch, Stewart, Kolasch & Birch, LLP

(57) ABSTRACT

Provided are: an aromatic sulfonium salt compound which exhibits low corrosion to a substrate and excellent photolithographic characteristics and is thus useful as a photoacid generator and as a cationic polymerization agent; and a photoacid generator, a resist composition, a cationic polymerization initiator and a cationically polymerizable agent composition, which include the aromatic sulfonium salt compound. The aromatic sulfonium salt compound is represented by the following Formula (I):

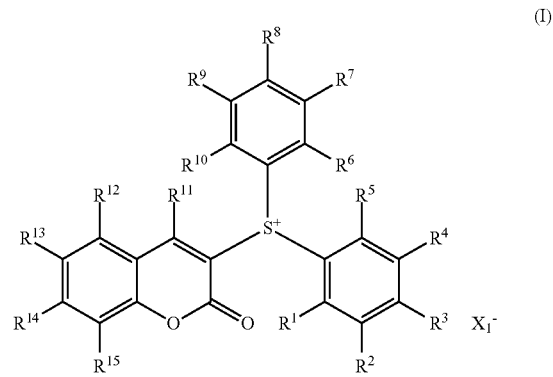

(wherein, $R^1$ to $R^{10}$ each independently represent a hydrogen atom, a halogen atom, a hydroxyl group, a nitro group, a cyano group, an alkyl group having 1 to 18 carbon atoms which is optionally substituted, or the like; $R^{11}$ to $R^{15}$ each independently represent a hydrogen atom, an alkoxy group having 1 to 18 carbon atoms which is optionally substituted, or the like; at least one of $R^{11}$ to $R^{15}$ is not a hydrogen atom; and $X_1^-$ represents a monovalent organic sulfonate anion).

9 Claims, No Drawings

(56) References Cited

FOREIGN PATENT DOCUMENTS

| JP | 4341406 B2 | 12/2012 |
| JP | 2013-061642 A | 4/2013 |
| JP | 2013-104985 A | 5/2013 |
| JP | 2014-094925 A | 5/2014 |
| JP | 2015-004961 A | 1/2015 |
| JP | 2015168617 * | 9/2015 |
| WO | WO 03/074509 A1 | 9/2003 |
| WO | WO 2011/052327 A1 | 5/2011 |

OTHER PUBLICATIONS

Written Opinion of the International Searching Authority for PCT/JP2015/058119 (PCT/ISA/237) dated May 19, 2015.
European Search Report issued in correponding European Application No. 15885452.1 and dated Jun. 21, 2018.

* cited by examiner

AROMATIC SULFONIUM SALT COMPOUND, PHOTOACID GENERATOR, RESIST COMPOSITION, CATIONIC POLYMERIZATION INITIATOR, AND CATIONICALLY POLYMERIZABLE COMPOSITION

TECHNICAL FIELD

The present invention relates to an aromatic sulfonium salt compound, a photoacid generator, a resist composition, a cationic polymerization initiator, and a cationically polymerizable composition. More particularly, the present invention relates to: an aromatic sulfonium salt compound which exhibits low corrosion to a substrate and excellent photolithographic characteristics and is useful as a photoacid generator and as a cationic polymerization agent; and a photoacid generator, a resist composition, a cationic polymerization initiator and a cationically polymerizable agent composition, which comprise the aromatic sulfonium salt compound.

BACKGROUND ART

Sulfonium salt compounds are substances that generate an acid when irradiated with an energy beam such as light, and they are used as, for example, photoacid generators in photolithography resist compositions used for the formation of electronic circuit such as a semiconductor, and cationic polymerization initiators contained in photopolymerizable compositions such as resin compositions for stereolithography, paints, coatings and adhesives.

With regard to sulfonium salt compounds, Patent Document 1 discloses a coumarin derivative; however, the coumarin derivative is disclosed as a hypoglycemic agent, and the Patent Document 1 merely describes that the coumarin derivative is useful for the treatment and prevention of diabetes and offers no description that the coumarin derivative may be used as a photoacid generator. In addition, Patent Document 2 discloses a cationic polymerization initiator which comprises a sulfonium salt having a coumarin skeleton, and Patent Document 3 discloses a heterocycle-containing sulfonium salt that is useful as, for example, a cationic photopolymerization initiator and an acid generator for chemically amplified resists. However, these Patent Documents suggest neither an alkoxy group nor an arylalkoxy group as a substituent of a coumarin skeleton, and do not indicate a structure which comprises sulfonium at the 3-position of a coumarin skeleton.

RELATED ART DOCUMENTS

Patent Documents

Patent Document 1: Japanese Unexamined Patent Application Publication No. H9-052891
Patent Document 2: Japanese Unexamined Patent Application Publication No. H11-035613
Patent Document 3: Japanese Patent No. 4341406

SUMMARY OF THE INVENTION

Problems to be Solved by the Invention

Resist compositions and cationically polymerizable compositions are laminated or coated on a substrate in the form of a film or a liquid. Therefore, in resist compositions, photoacid generators used in cationically polymerizable compositions and cationically polymerizable compositions themselves, low corrosiveness to the substrate and excellent photolithographic characteristics are demanded. However, the relationships between this point and the type and position of a substituent are not sufficiently examined in Patent Documents 1 to 3.

In view of the above, an object of the present invention is to provide an aromatic sulfonium salt compound which exhibits low corrosion to a substrate and excellent photolithographic characteristics and is thus useful as a photoacid generator and as a cationic polymerization agent; and a photoacid generator, a resist composition, a cationic polymerization initiator and a cationically polymerizable agent composition, which comprise the aromatic sulfonium salt compound.

Means for Solving the Problems

The present inventors intensively studied to solve the above-described problems and consequently discovered that the problems can be solved by a photoacid generator and a cationic polymerization initiator which comprise an aromatic sulfonium salt compound that contains an organic sulfonate anion having a prescribed structure, thereby completing the present invention.

That is, the aromatic sulfonium salt compound of the present invention is characterized in that it is represented by the following Formula (I):

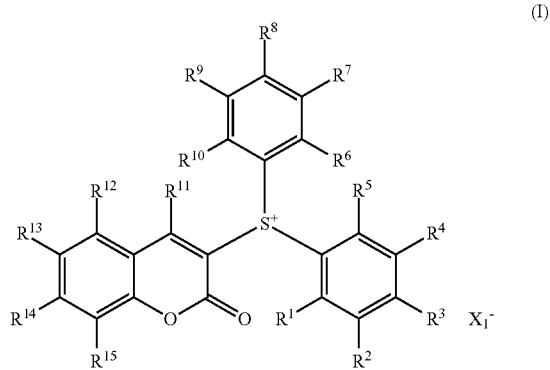

(wherein, $R^1$ to $R^{10}$ each independently represent a hydrogen atom, a halogen atom, a hydroxyl group, a nitro group, a cyano group, an alkyl group having 1 to 18 carbon atoms which is optionally substituted, an aryl group having 6 to 20 carbon atoms which is optionally substituted, or an arylalkyl group having 7 to 20 carbon atoms which is optionally substituted; methylene chains in the alkyl group having 1 to 18 carbon atoms, the aryl group having 6 to 20 carbon atoms and the arylalkyl group having 7 to 20 carbon atoms, which groups are represented by $R^1$ to $R^{10}$, are optionally interrupted by —O—, —S—, —CO—, —CO—O— or —O—CO—; $R^{11}$ to $R^{15}$ each independently represent a hydrogen atom, an alkoxy group having 1 to 18 carbon atoms which is optionally substituted, an arylalkoxy group having 7 to 20 carbon atoms which is optionally substituted, a thioalkyl group having 1 to 18 carbon atoms which is optionally substituted, an arylthioalkyl group having 7 to 20 carbon atoms which is optionally substituted, or —NRR'; R and R' each independently represent a hydrogen atom, an alkyl group having 1 to 10 carbon atoms, or an aryl group having 6 to 12 carbon atoms; at least one of $R^{11}$ to $R^{15}$ is not a hydrogen atom; and $X_1^-$ represents a monovalent organic sulfonate anion).

Further, another aromatic sulfonium salt compound of the present invention is characterized in that it is represented by the following Formula (II):

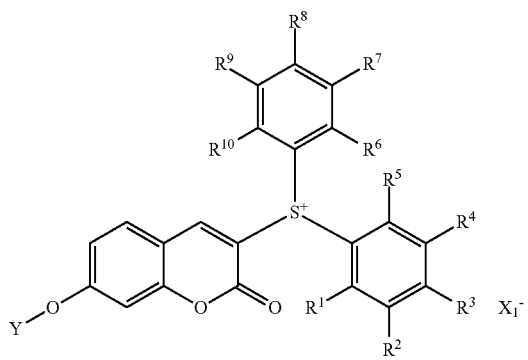

(II)

(wherein, $R^1$ to $R^{10}$ and $X_1^-$ are the same as in the Formula (I); and Y represents an alkyl group having 1 to 18 carbon atoms or an arylalkyl group having 7 to 20 carbon atoms).

The photoacid generator of the present invention is characterized by comprising the aromatic sulfonium salt compound of the present invention.

The resist composition of the present invention is characterized by comprising the photoacid generator of the present invention.

The resist composition of the present invention is preferably a positive or negative resist composition for i-line.

The cationic polymerization initiator of the present invention is characterized by comprising the aromatic sulfonium salt compound of the present invention.

The cationically polymerizable composition of the present invention is characterized by comprising the cationic polymerization initiator of the present invention.

Effects of the Invention

According to the present invention, an aromatic sulfonium salt compound which exhibits low corrosion to a substrate and excellent photolithographic characteristics and is thus useful as a photoacid generator and as a cationic polymerization agent; and a photoacid generator, a resist composition, a cationic polymerization initiator and a cationically polymerizable agent composition, which comprise the aromatic sulfonium salt compound, can be provided.

MODE FOR CARRYING OUT THE INVENTION

The present invention will now be described in detail based on preferred embodiments.

The aromatic sulfonium salt compound of the present invention is represented by the following Formula (I):

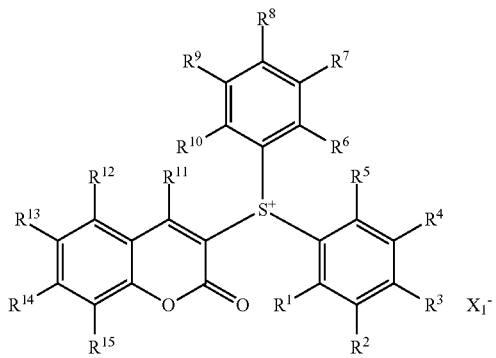

(I)

(wherein, $R^1$ to $R^{10}$ each independently represent a hydrogen atom, a halogen atom, a hydroxyl group, a nitro group, a cyano group, an alkyl group having 1 to 18 carbon atoms which is optionally substituted, an aryl group having 6 to 20 carbon atoms which is optionally substituted, or an arylalkyl group having 7 to 20 carbon atoms which is optionally substituted; methylene chains in the alkyl group having 1 to 18 carbon atoms, the aryl group having 6 to 20 carbon atoms and the arylalkyl group having 7 to 20 carbon atoms, which groups are represented by $R^1$ to $R^{10}$, are optionally interrupted by —O—, —S—, —CO—, —CO—O— or —O—CO—; $R^{11}$ to $R^{15}$ each independently represent a hydrogen atom, an alkoxy group having 1 to 18 carbon atoms which is optionally substituted, an arylalkoxy group having 7 to 20 carbon atoms which is optionally substituted, a thioalkyl group having 1 to 18 carbon atoms which is optionally substituted, an arylthioalkyl group having 7 to 20 carbon atoms which is optionally substituted, or —NRR'; R and R' each independently represent a hydrogen atom, an alkyl group having 1 to 10 carbon atoms, or an aryl group having 6 to 12 carbon atoms; at least one of $R^{11}$ to $R^{15}$ is not a hydrogen atom; and $X_1^-$ represents a monovalent organic sulfonate anion).

Examples of the halogen atom represented by $R^1$ to $R^{10}$ in the Formula (I) include fluorine, chlorine, bromine, and iodine.

Examples of the alkyl group having 1 to 18 carbon atoms which is optionally substituted and represented by $R^1$ to $R^{10}$ in the Formula (I) include methyl, ethyl, propyl, isopropyl, butyl, s-butyl, t-butyl, isobutyl, pentyl, isopentyl, t-pentyl, hexyl, cyclohexyl, isohexyl, 2-ethylhexyl, heptyl, octyl, nonyl, decyl, undecyl, dodecyl, tridecyl, isotridecyl, tetradecyl, hexadecyl, heptadecyl, octadecyl, 1-adamantyl, 2-adamantyl, 2-methyl-1-adamantyl, 2-methyl-2-adamantyl, 2-ethyl-1-adamantyl, 2-ethyl-2-adamantyl, 2-norbornyl, 2-norbornylmethyl, vinyl, allyl, isopropenyl, 1-propenyl, fluoromethyl, difluoromethyl, trifluoromethyl, chloromethyl, dichloromethyl, trichloromethyl, bromomethyl, dibromomethyl, tribromomethyl, difluoroethyl, trichloroethyl, dichlorodifluoroethyl, pentafluoroethyl, heptafluoropropyl, nonafluorobutyl, decafluoropentyl, tridecafluorohexyl, pentadecafluoroheptyl, heptadecafluorooctyl, cyanomethyl, and hydroxymethyl.

Examples of the aryl group having 6 to 20 carbon atoms which is optionally substituted and represented by $R^1$ to $R^{10}$ in the Formula (I) include phenyl, naphthyl, 2-methylphenyl, 3-methylphenyl, 4-methylphenyl, 4-vinylphenyl, 3-isopropylphenyl, 4-isopropylphenyl, 4-butylphenyl, 4-isobutylphenyl, 4-t-butylphenyl, 4-hexylphenyl, 4-cyclohexylphenyl, 4-octylphenyl, 4-(2-ethylhexyl)phenyl, 4-stearylphenyl, 2,3-dimethylphenyl, 2,4-dimethylphenyl, 2,5-dimethylphenyl, 2,6-dimethylphenyl, 3,4-dimethylphenyl, 3,5-dimethylphenyl, 2,4-di-t-butylphenyl, cyclohexylphenyl, and hydroxyphenyl.

Examples of the arylalkyl group having 7 to 20 carbon atoms which is optionally substituted and represented by $R^1$ to $R^{10}$ in the Formula (I) include benzyl, phenethyl, phenacyl, 2-phenylpropan-2-yl, diphenylmethyl, triphenylmethyl, styryl, cinnamyl, 2-hydroxybenzyl, 2-hydroxyphenethyl, 2-hydroxyphenacyl, 2-phenoxyethyl, and 2-phenylthioethyl.

Specific examples of a substituent that can substitute the alkyl group having 1 to 18 carbon atoms which is optionally substituted, the aryl group having 6 to 20 carbon atoms which is optionally substituted and the arylalkyl group having 7 to 20 carbon atoms which is optionally substituted, all of which groups are represented by $R^1$ to $R^{10}$, include alkyl groups, such as methyl, ethyl, propyl, isopropyl, butyl, isobutyl, t-butyl, pentyl, isopentyl, t-pentyl, neopentyl, hexyl, isohexyl, heptyl, octyl, 2-ethylhexyl, nonyl, decyl, undecyl, dodecyl, tridecyl, isotridecyl, myristyl, palmityl, stearyl, cyclopropyl, cyclohexyl, 1-adamantyl, 2-adamantyl, 2-methyl-1-adamantyl, 2-methyl-2-adamantyl, 2-ethyl-1-adamantyl, 2-ethyl-2-adamantyl, 2-norbornyl, 2-norbornylmethyl, camphor-10-yl, vinyl, allyl, isopropenyl, 1-propenyl, 2-methoxy-1-propenyl, fluoromethyl, difluoromethyl, trifluoromethyl, chloromethyl, dichloromethyl, trichloromethyl, bromomethyl, dibromomethyl, tribromomethyl, difluoroethyl, trichloroethyl, dichlorodifluoroethyl, pentafluoroethyl, heptafluoropropyl, nonafluorobutyl, decafluoropentyl, tridecafluorohexyl, pentadecafluoroheptyl, heptadecafluorooctyl, methoxymethyl, methoxyethoxymethyl, methylthiomethyl, ethoxyethyl, butoxymethyl, t-butylthiomethyl, 4-pentenyloxymethyl, trichloroethoxymethyl, bis(2-chloroethoxy)methyl, methoxycyclohexyl, 1-(2-chloroethoxy)ethyl, methoxyethyl, 1-methyl-1-methoxyethyl, ethyldithioethyl, trimethyl silylethyl, t-butyldimethylsilyloxymethyl, 2-(trimethyl silyl) ethoxymethyl, t-butoxycarbonylmethyl, ethyloxycarbonylmethyl, ethylcarbonylmethyl, t-butoxycarbonylmethyl, acryloyloxyethyl, methacryloyloxyethyl, 2-methyl-2-adamantyloxycarbonylmethyl and acetylethyl; aryl groups, such as phenyl, 1-naphthyl, 2-naphthyl, anthracene-1-yl, phenanthrene-1-yl, o-tolyl, m-tolyl, p-tolyl, 4-vinylphenyl, ethylphenyl, propylphenyl, 3-isopropylphenyl, 4-isopropylphenyl, 4-butylphenyl, 4-isobutylphenyl, 4-t-butylphenyl, 4-hexylphenyl, 4-cyclohexylphenyl, 4-octylphenyl, 4-(2-ethylhexyl)phenyl, 2,3-dimethylphenyl, 2,4-dimethylphenyl, 2,5-dimethylphenyl, 2,6-dimethylphenyl, 3,4-dimethylphenyl, 3,5-dimethylphenyl, 2,4-di-t-butylphenyl, 2,5-di-t-butylphenyl, 2,6-di-t-butylphenyl, 2,4-di-t-pentylphenyl, 2,5-di-t-pentylphenyl, cyclohexylphenyl, biphenylyl, 2,4,5-trimethylphenyl, 9-fluorenyl, 4-chlorophenyl, 3,4-dichlorophenyl, 4-trichlorophenyl, 4-trifluorophenyl, fluorophenyl, trifluoromethylphenyl, pentafluorophenyl, heptafluoro-p-tolyl, 4-formylphenyl, 4-nitrophenyl, ethoxynaphthyl, 4-fluoromethylphenyl, 4-methoxyphenyl and 2,4-dinitrophenyl; arylalkyl groups, such as benzyl, methylbenzyl, dimethylbenzyl, trimethylbenzyl, phenylbenzyl, diphenylmethyl, triphenylmethyl, 2-phenylethyl, 2-phenylpropyl, styryl, cinnamyl, fluorobenzyl, chlorobenzyl, bromobenzyl, cyanobenzyl, dichlorobenzyl, methoxybenzyl, dimethoxybenzyl, benzyloxymethyl, methoxybenzyloxymethyl, 1-methyl-1-benzyloxyethyl, 1-methyl-1-benzyloxy-2-fluoroethyl, guaiacolmethyl, phenoxymethyl, phenylthiomethyl, nitrobenzyl, dinitrobenzhydryl, dibenzosuberyl, (phenyldimethylsilyl)methoxymethyl, phenyl sulfonylethyl, triphenylphosphonioethyl, triphenylmethoxymethyl, phenacyl and bromophenacyl; alkoxy groups represented by RO—, acyl groups represented by RCO—, ester groups represented by RCOO— or ROCO—, carbonate groups represented by ROCOO—, sulfanyl groups represented by RS—, sulfinyl groups represented by RSO—, sulfonyl groups represented by $RSO_2$—, and sulfonic acid ester groups represented by $RSO_3$—, wherein R represents any of the above-described alkyl groups, aryl groups, arylalkyl groups, and heterocyclic groups such as tetrahydropyranyl, 3-bromotetrahydropyranyl, tetrahydrothiopyranyl, methoxytetrahydropyranyl, methoxytetrahydrothiopyranyl, 4-methoxytetrahydrothiopyran-S, S-dioxide-4-yl, 1-[(2-chloro-4-methyl)phenyl]-4-methoxypiperidin-4-yl, 1,4-dioxan-2-yl, tetrahydrofuranyl, tetrahydrothiofuranyl, 2,3,3a,4,5,6,7,7a-octahydro-7,8,8-trimethyl-4,7-metanobenzofuran-2-yl, 2-pyridylmethyl, 4-pyridylmethyl, 3-picolin-N-oxide-2-ylmethyl, 1,3-benzodithioranyl, benzisothiazolin-S,S-dioxide-3-yl and tetrafluoro-4-pyridyl; a formyl group; a carboxyl group; a formyloxy group; a sulfo group; silyloxy groups, such as trimethylsilyloxy, triethylsilyloxy, tripropylsilyloxy, dimethylpropylsilyloxy, diethylpropylsilyloxy, dimethyl(1,1,2,2-tetramethyl)ethylsilyloxy, butyldimethylsilyloxy, butyldiphenylsilyloxy, tribenzylsilyloxy, trixylylsilyloxy, triphenylsilyloxy, diphenylmethyl silyloxy and butylmethoxyphenylsilyloxy; a phosphoric acid ester group; benzylthiocarbonate; methyldithiocarbonate; a hydroxyl group; a nitro group; a cyano group; and halogen atoms, such as fluorine, chlorine, bromine and iodine.

In the alkyl group having 1 to 18 carbon atoms which is optionally substituted, the aryl group having 6 to 20 carbon atoms which is optionally substituted and the arylalkyl group having 7 to 20 carbon atoms which is optionally substituted, all of which groups are represented by $R^1$ to $R^{10}$, methylene chains may be interrupted by —O—, —S—, —CO—, —CO—O— or —O—CO—.

Examples of the alkoxy group having 1 to 18 carbon atoms which is optionally substituted and represented by $R^{11}$ to $R^{15}$ in the Formula (I) include methoxy, ethoxy, propyloxy, isopropyloxy, butyloxy, s-butyloxy, t-butyloxy, isobutyloxy, pentyloxy, isopentyloxy, t-pentyloxy, hexyloxy, heptyloxy, octyloxy, 2-ethylheptyloxy, cyclohexyloxy, cyclohexylmethyloxy, tetrahydrofuranyloxy, and tetrahydropyranyloxy. These alkoxy groups may be substituted with a hydroxyl group, a nitro group, a cyano group and/or a halogen atom such as fluorine, chlorine, bromine or iodine.

Examples of the arylalkoxy group having 7 to 20 carbon atoms which is optionally substituted and represented by $R^{11}$ to $R^{15}$ in the Formula (I) include benzyloxy, phenethyloxy, phenylpropyloxy, phenacyloxy, diphenylmethyloxy, and triphenylmethyloxy. These arylalkoxy groups may be substituted with a hydroxyl group, a nitro group, a cyano group and/or a halogen atom such as fluorine, chlorine, bromine or iodine.

Examples of the thioalkyl group having 1 to 18 carbon atoms which is optionally substituted and represented by $R^{11}$ to $R^{15}$ in the Formula (I) include methylthio, ethylthio, propylthio, isopropylthio, butylthio, s-butylthio, t-butylthio, isobutylthio, pentylthio, isopentylthio, t-pentylthio, hexylthio, heptylthio, octylthio, 2-ethylheptylthio, cyclohexylthio, cyclohexylmethylthio, and tetrahydrothienyl. These thioalkyl groups may be substituted with a hydroxyl group, a nitro group, a cyano group and/or a halogen atom such as fluorine, chlorine, bromine or iodine.

Examples of the arylthioalkyl group having 7 to 20 carbon atoms which is optionally substituted and represented by $R^{11}$ to $R^{15}$ in the Formula (I) include benzylthio, phenethylthio, phenylpropylthio, phenacylthio, diphenylmethylthio, and triphenylmethylthio. These arylthioalkyl groups may be substituted with a hydroxyl group, a nitro group, a cyano group and/or a halogen atom such as fluorine, chlorine, bromine or iodine.

In —NRR' represented by $R^{11}$ to $R^{15}$ in the Formula (I), R and R' each independently represent a hydrogen atom, an alkyl group having 1 to 10 carbon atoms, or an aryl group having 6 to 12 carbon atoms. Examples of the alkyl group having 1 to 10 carbon atoms which is represented by R and R' include, among those alkyl groups exemplified above for the alkyl group having 1 to 18 carbon atoms which is represented by $R^1$ to $R^{10}$, ones having 1 to 10 carbon atoms, and examples of the aryl group having 6 to 12 carbon atoms which is represented by R and R' include, among those aryl groups exemplified above for the aryl group having 6 to 20 carbon atoms which is represented by $R^1$ to $R^{10}$, ones having 6 to 12 carbon atoms. Further, R and R' may be bound with each other to form a ring.

Examples of the organic sulfonate anion represented by $X_1^-$ in the Formula (I) include a methanesulfonate anion, a fluorosulfonate anion, a benzenesulfonate anion, a toluenesulfonate anion, a 1-naphthylsulfonate anion, a 2-naphthylsulfonate anion, a trifluoromethanesulfonate anion, a pentafluoroethanesulfonate anion, a heptafluoropropanesulfonate anion, a nonafluorobutanesulfonate anion, an undecafluoropentanesulfonate anion, a tridecafluorohexanesulfonate anion, a pentadecafluoroheptanesulfonate anion, heptadecafluorooctanesulfonate anion, a perfluoro-4-ethylcyclohexanesulfonate anion, an N-alkyl (or aryl) diphenylamine-4-sulfonate anion, a 2-amino-4-methyl-5-chlorobenzenesulfonate anion, a 2-amino-5-nitrobenzenesulfonate anion, those sulfonate anions described in Japanese Unexamined Patent Application Publication No. 2004-53799, a camphor sulfonate anion, a fluorobenzenesulfonate anion, a difluorobenzenesulfonate anion, a trifluorobenzenesulfonate anion, a tetrafluorobenzenesulfonate anion, a pentafluorobenzenesulfonate anion, 1,3,5-trimethylbenzenesulfonate, and 1,3,5-triisopropylbenzenesulfonate, as well as alkylsulfonate anions, fluoro-substituted alkylsulfonate anions, and alkylsulfonate imides and fluoro-substituted alkylsulfone imides which are substituted with an acryloyloxy group, a methacryloyloxy group, or an alicyclic alkyl group such as a norbornyl group or an adamantyl group. Among these organic sulfonate anions, from the standpoints of safety and solubility, a toluenesulfonate anion or a fluoro-substituted alkylsulfonate anion is preferred.

Among those compounds represented by the Formula (I), a compound represented by the following Formula (II) is preferred since it yields a photoacid generator which is highly soluble in solvents and compatible with resins and exhibits excellent developing properties:

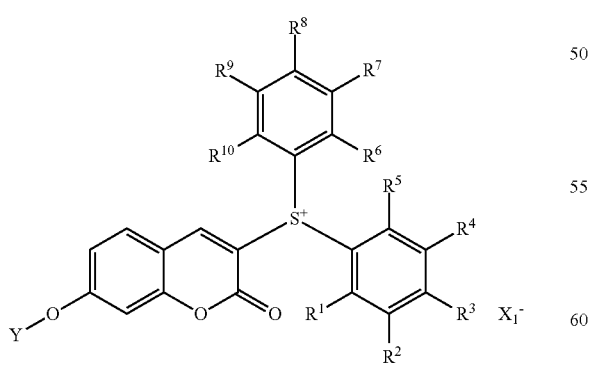

(II)

(wherein, $R^1$ to $R^{10}$ and $X_1^-$ are the same as in the Formula (I); and Y represents an alkyl group having 1 to 18 carbon atoms or an arylalkyl group having 7 to 20 carbon atoms).

Specific examples of the aromatic sulfonium salt compound represented by the Formula (I) include the following structures.

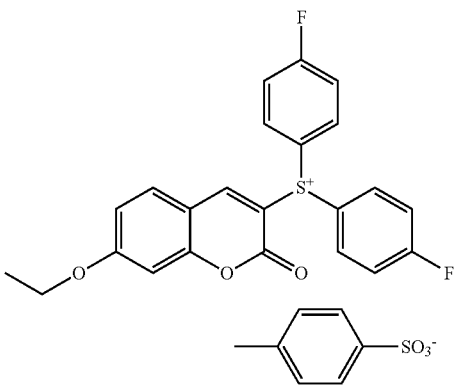

Compound No. 1

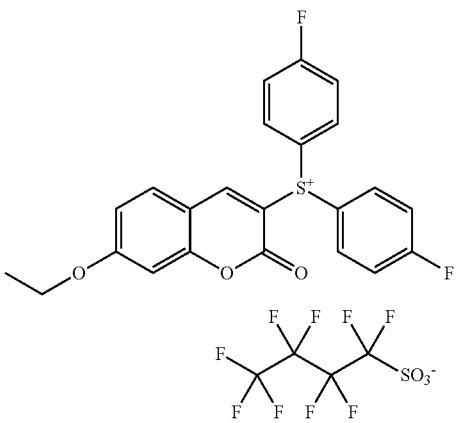

Compound No. 2

Compound No. 3

-continued
Compound No. 4
Compound No. 5
Compound No. 6
Compound No. 7
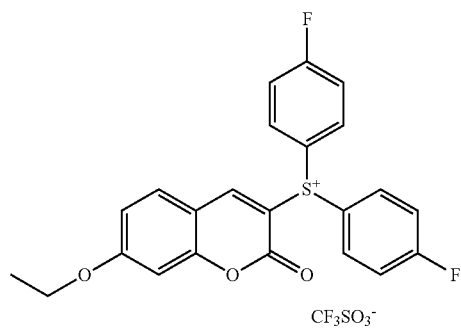
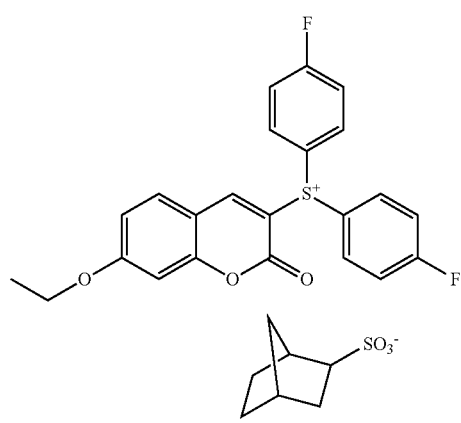
Compound No. 8
Compound No. 9
Compound No. 10
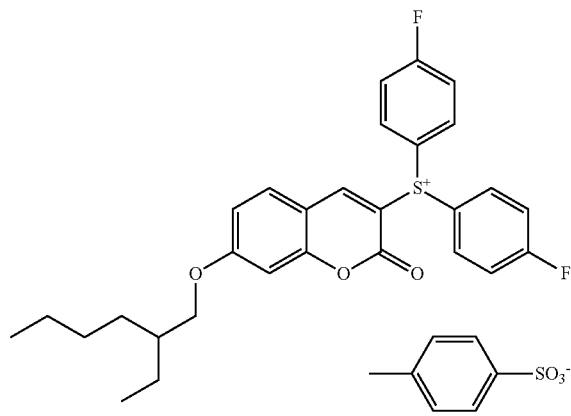
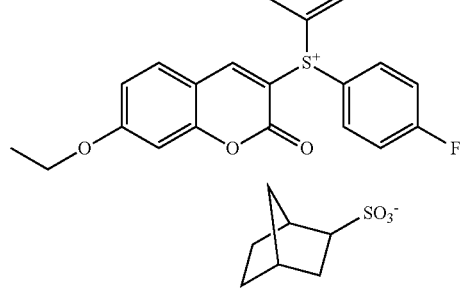

Compound No. 11
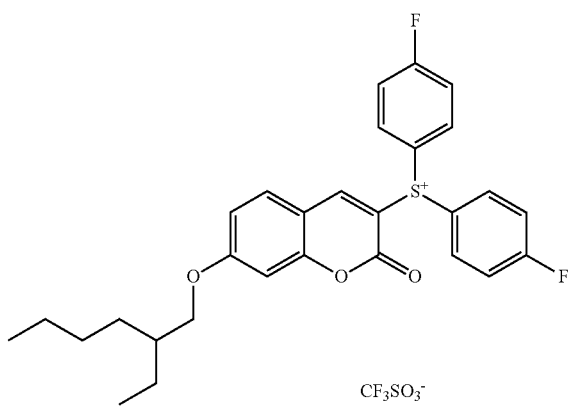
Compound No. 14
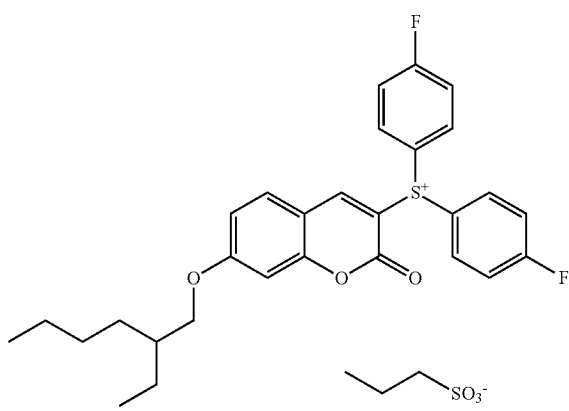
Compound No. 12
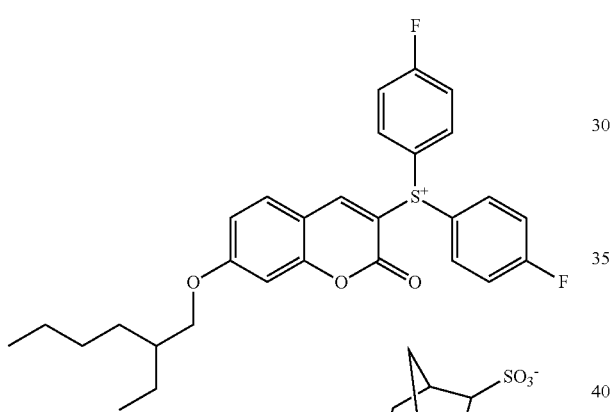
Compound No. 15
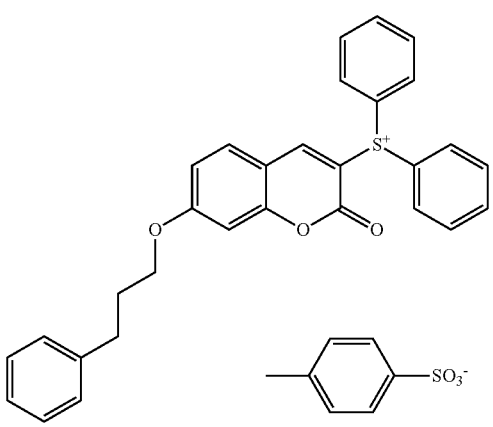
Compound No. 13
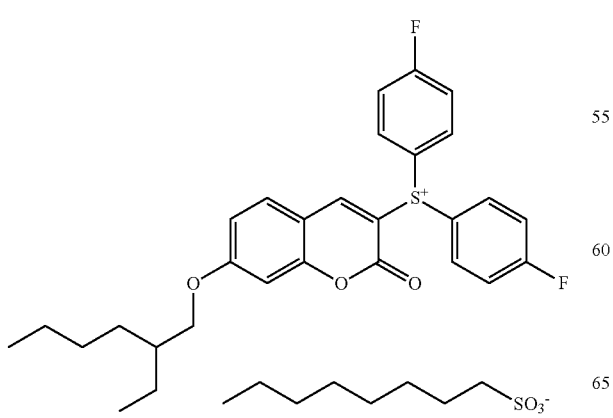
Compound No. 16
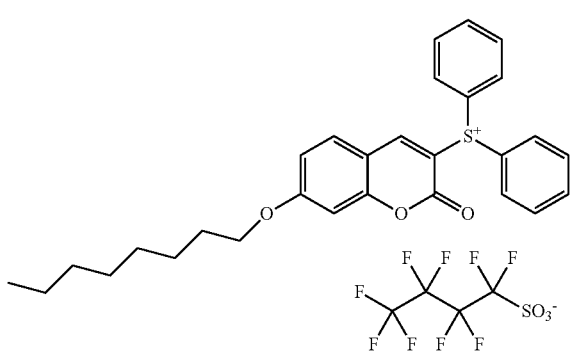

Compound No. 17
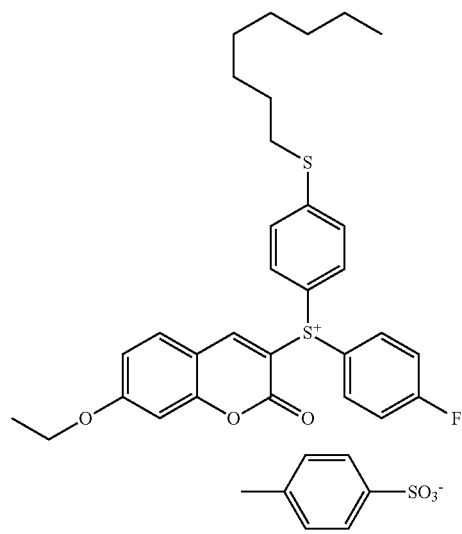
Compound No. 18
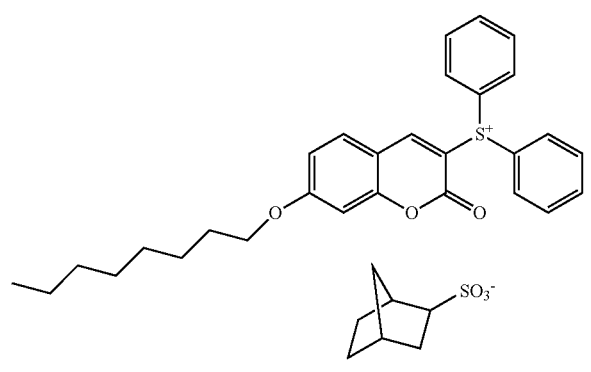
Compound No. 19
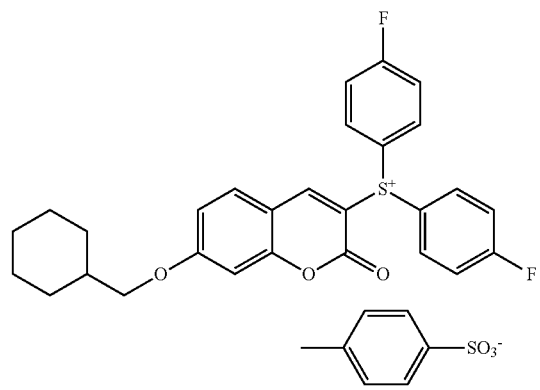
Compound No. 20
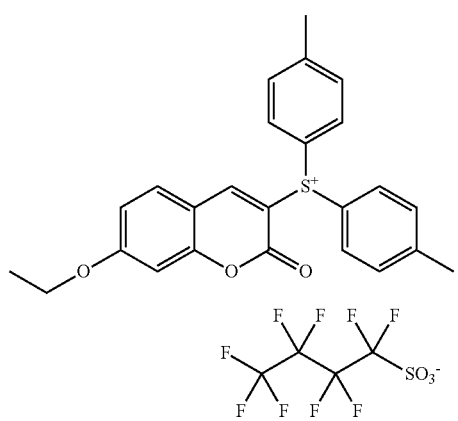
Compound No. 21
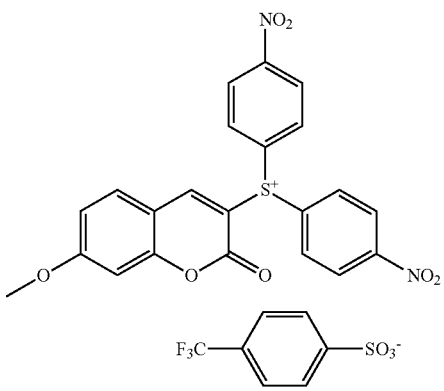
Compound No. 22
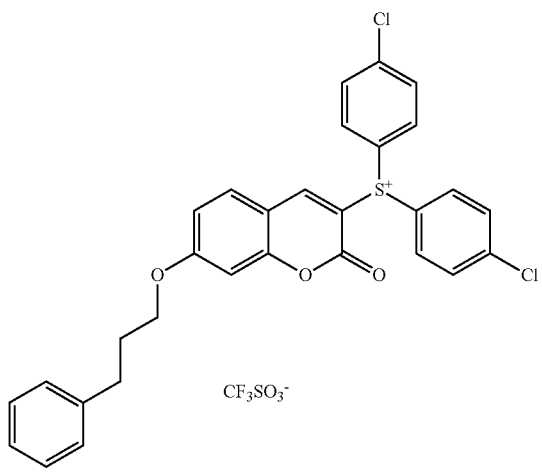

Compound No. 23
Compound No. 26
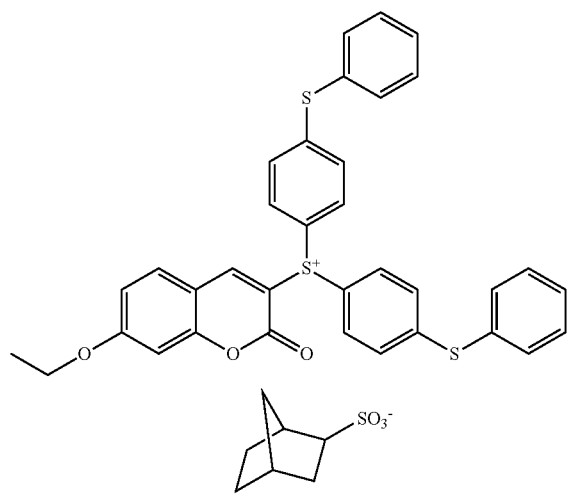
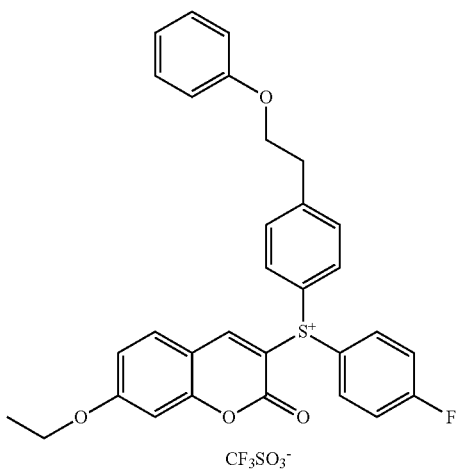
Compound No. 24
Compound No. 27
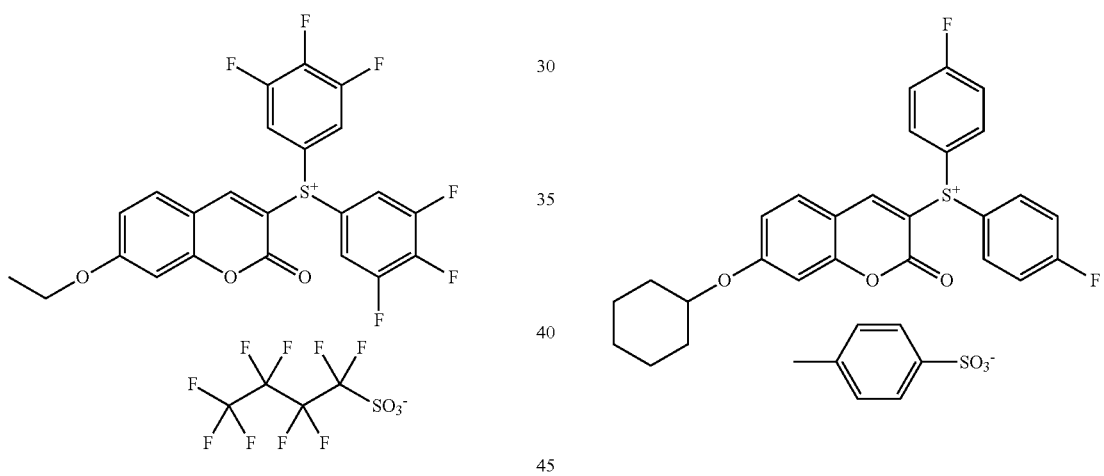
Compound No. 25
Compound No. 28
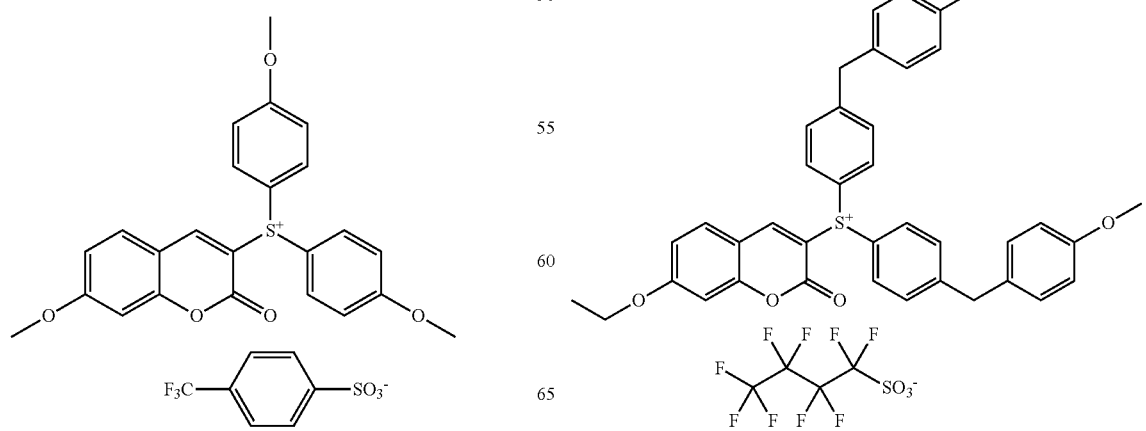

-continued
Compound No. 29
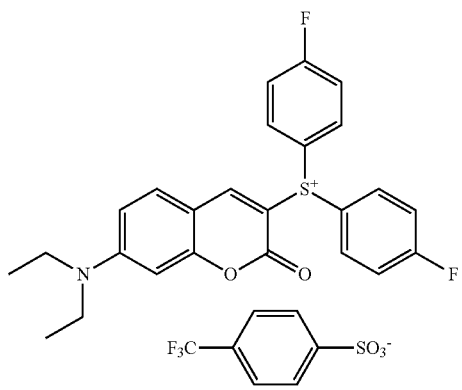
Compound No. 30
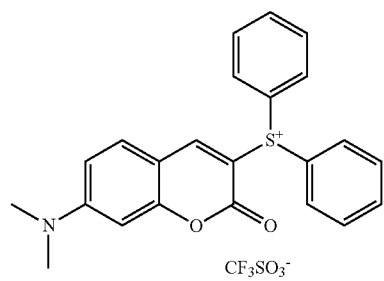
Compound No. 31
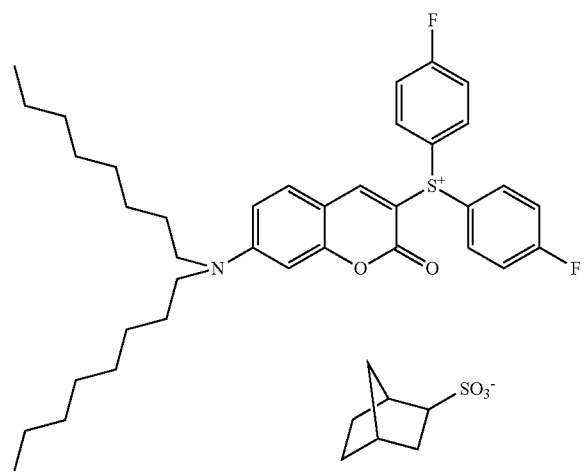
Compound No. 32
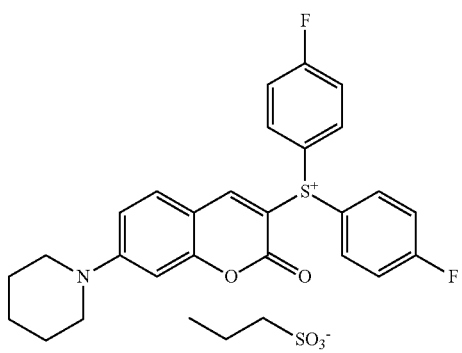
-continued
Compound No. 33
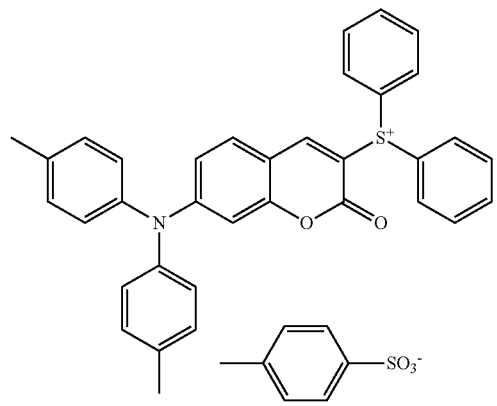
Compound No. 34
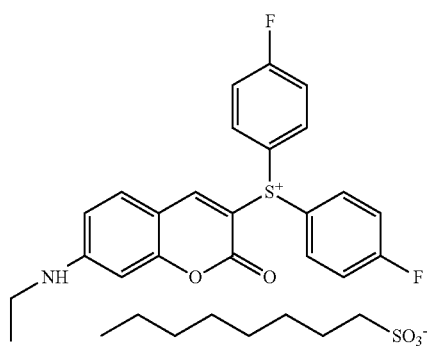
Compound No. 35
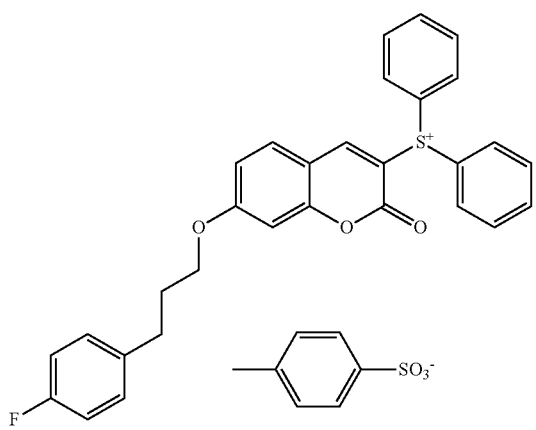

Compound No. 36
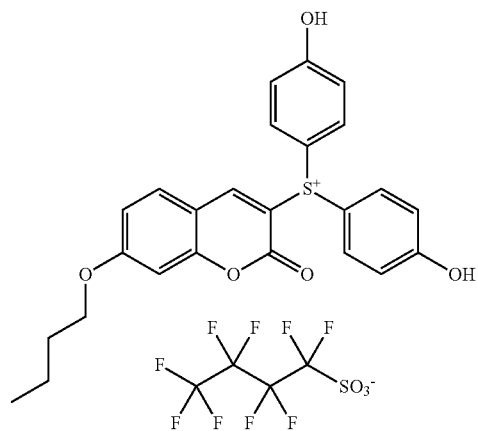
Compound No. 37
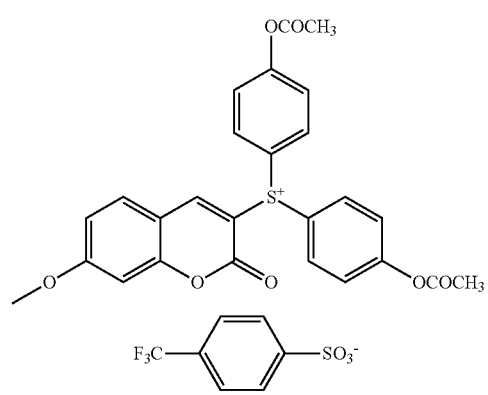
Compound No. 38
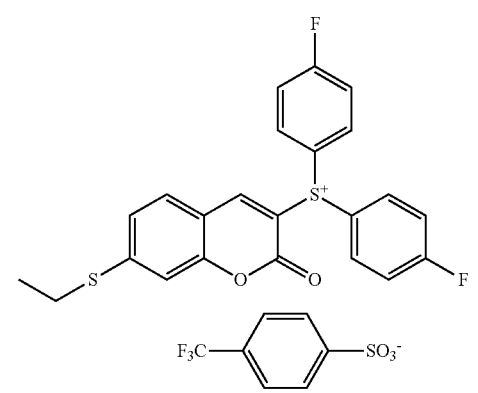
Compound No. 39
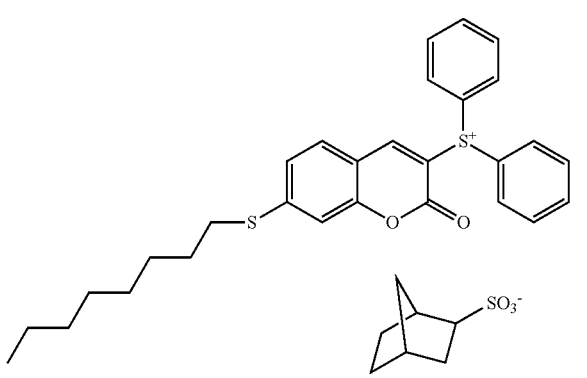
Compound No. 40
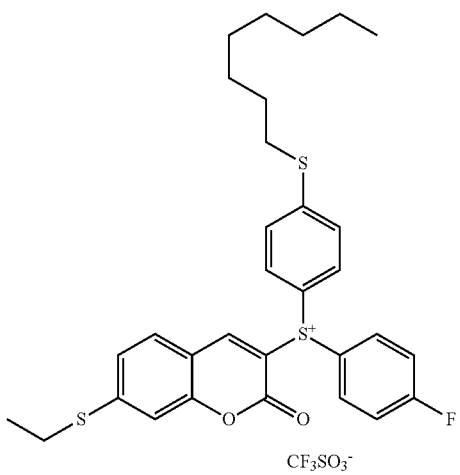
Compound No. 41
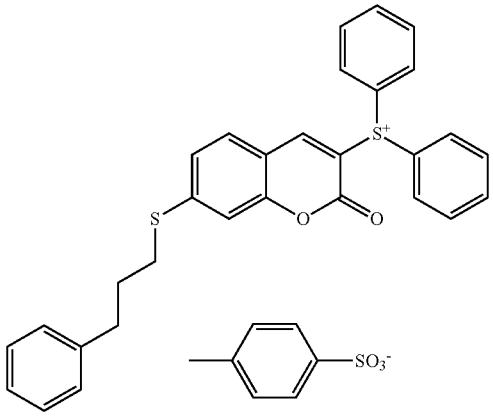
Compound No. 42
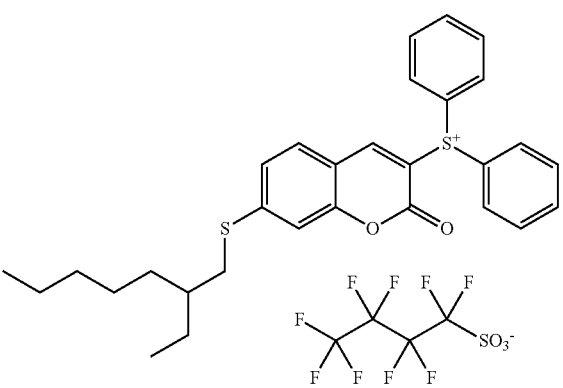

Compound No. 43

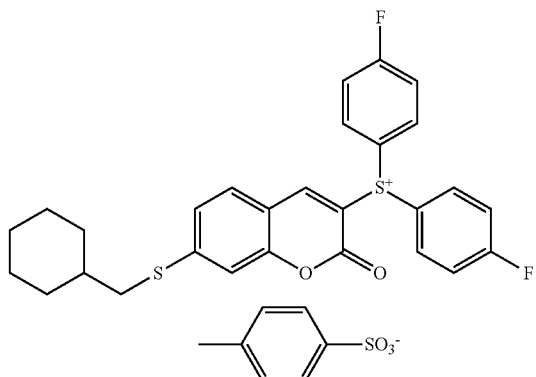

Compound No. 44

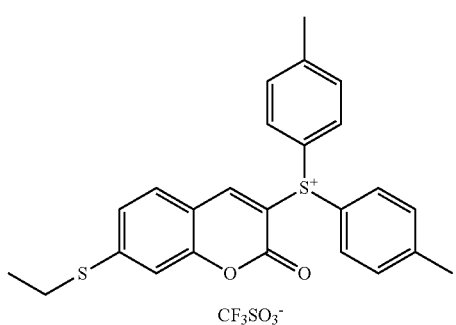

Compound No. 45

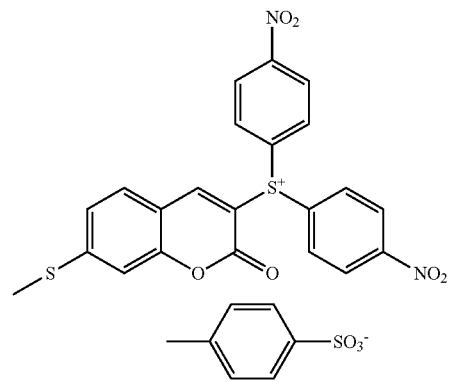

Compound No. 46

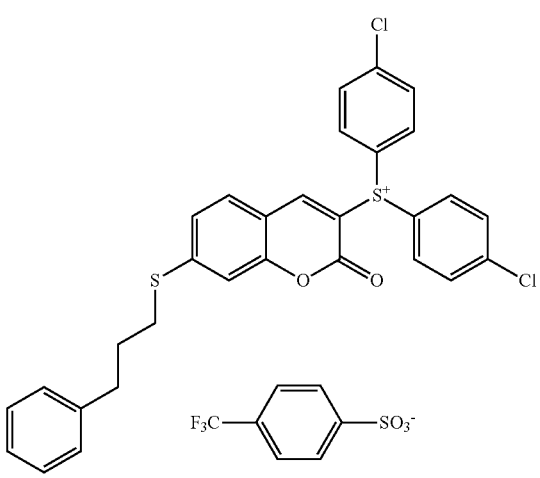

Compound No. 47

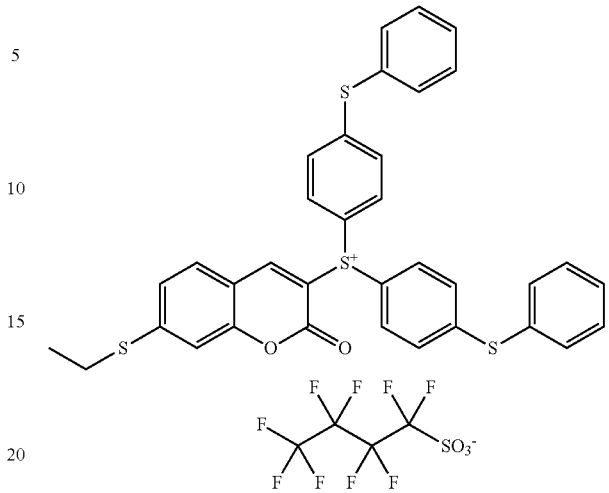

Compound No. 48

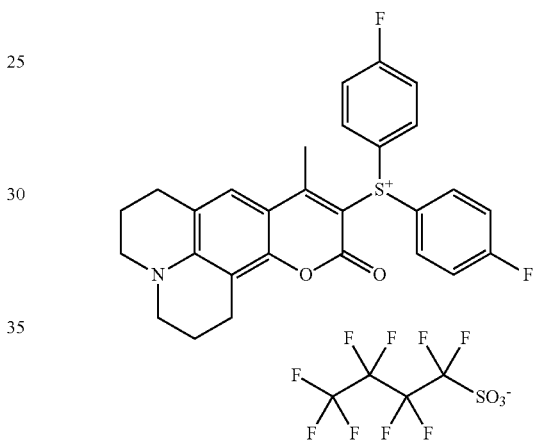

Among those aromatic sulfonium salt compounds represented by the Formula (I), ones which generate an acid species having a Hammett acidity function ($H_0$) of not less than −17 after being photodegraded are preferred since such aromatic sulfonium salt compounds yield a fine pattern. The Hammett acidity function ($H_0$) is a numerical value that quantitatively indicates the acid-base strength of a solution, and it is used for measuring the pH of a strong acidic solution in particular. The Hammett acidity function ($H_0$) is represented by the following equation (b) with respect to the following equation (a).

$$H^+ + B \rightleftharpoons HB^+ \quad (a)$$

$$H_0 = pKa + \log([B]/[BH^+]) \quad (b)$$

As a method of measuring the Hammett acidity function ($H_0$), a variety of methods are known, and examples thereof include an ammonia temperature-programmed desorption method (TPD method) and a method using a Hammett indicator in accordance with the method described in "Advances in Catalysis" (volume 37, pp. 186-187).

The aromatic sulfonium salt compound of the present invention has a property of releasing a Lewis acid when irradiated with an active energy beam, such as a deep ultraviolet ray (e.g., EUV (Extreme Ultra-Violet), X-ray, $F_2$, ArF, KrF, i-line, h-line or g-line), an electron beam, a radioactive ray or a high-frequency wave, and is capable of acting on an acid-reactive organic substance to induce decomposition or polymerization thereof. The aromatic sulfonium salt compound of the present invention is thus useful as a photoacid generator of a positive or negative photoresist and as a cationic polymerization initiator used in a wide range of applications, including photoresists for the preparation of lithographic plates, letterpress printing plates, printed circuit boards, ICs or LSIs, image formation such as relief image formation and image replication, and photocurable inks, paints, adhesives and the like.

Next, the photoacid generator of the present invention will be described.

The photoacid generator of the present invention comprises the aromatic sulfonium salt compound of the present invention. The photoacid generator of the present invention can be used for, for example, cleaving a chemical bond of an ester group, an ether group or the like in acid-reactive organic substances or acrylic resins. When the photoacid generator of the present invention is used for an acid-reactive organic substance, the amount thereof is not particularly restricted; however, it is preferably 0.01 to 100 parts by mass, more preferably 0.05 to 20 parts by mass, with respect to 100 parts by mass of the acid-reactive organic substance. When the amount of the photoacid generator is less than 0.01 parts by mass, the sensitivity and the developability may be deteriorated, whereas when the amount is greater than 20 parts by mass, the transparency to radiation is reduced, which can makes it difficult to obtain a rectangular resist pattern. It is noted here, however, that the photoacid generator of the present invention may be used in an amount that is greater or less than the above-described range, depending on the factors such as the properties of the acid-reactive organic substance, the light irradiation intensity, the time required for reaction, the physical properties and the cost.

Next, the resist composition of the present invention will be described.

The resist composition of the present invention comprises the aromatic sulfonium salt compound of the present invention as an indispensable photoacid generator along with a resin whose solubility in a developing solution changes with the action of an acid (hereinafter, such a resin is also referred to as "resist base resin"). The resist composition of the present invention is particularly useful as a chemically amplified resist. There are two types of chemically amplified resists: positive resists which are made soluble in a developing solution through a polarity change induced by a deprotection reaction of the side chain of a resist base resin, such as cleavage of a chemical bond of an ester group, an acetal group or the like, which is attributed to the action of an acid generated from a photoacid generator upon exposure; and negative resists which undergoes a chemical chain reaction such as polymerization or cross-linking and is made insoluble in a developing solution by a cross-linking reaction or polarity change of a resist base resin and from which only unexposed parts are selectively removed upon development. In the present invention, such a resist base resin may be used individually, or two or more thereof may be used in combination.

The resist base resin used in the resist composition of the present invention is not particularly restricted; however, it preferably has a structure which has a small extinction coefficient for the wavelength of active energy beam and exhibits high etching resistance.

Examples of the resist base resin include polyhydroxystyrenes and derivatives thereof; polyacrylic acids and derivatives thereof; polymethacrylic acids and derivatives thereof; copolymers formed by two or more selected from hydroxystyrene, acrylic acid, methacrylic acid and derivatives thereof; copolymers formed by two or more selected from hydroxystyrene, styrene and derivatives thereof; copolymers formed by three or more selected from polyolefins and derivatives thereof, cycloolefins and derivatives thereof, maleic anhydride, and acrylic acid and derivatives thereof; copolymers formed by three or more selected from cycloolefins and derivatives thereof, maleimide, and acrylic acid and derivatives thereof; polynorbornenes; high-molecular-weight polymers of one or more selected from the group consisting of metathesis ring-opening polymers; and silicone resins.

Detailed specific examples of the resist base resin are disclosed in, for example, Claims 8 to 11 of Japanese Unexamined Patent Application Publication No. 2003-192665, Claim 3 of Japanese Unexamined Patent Application Publication No. 2004-323704, Japanese Unexamined Patent Application Publication No. H10-10733, Japanese Unexamined Patent Application Publication No. 2010-15079, and Japanese Unexamined Patent Application Publication No. 2010-15101.

The polystyrene-equivalent weight-average molecular weight (Mw) of the resist base resin, which is determined by gel permeation chromatography (GPC), is usually 1,500 to 300,000, preferably 2,000 to 200,000, more preferably 3,000 to 100,000. In this case, when the Mw of the resist base resin is less than 1,500, the resist base resin tends to show a reduced heat resistance as a resist, whereas when the Mw is higher than 300,000, the developability and coatability of the resist base resin as a resist tends to be deteriorated.

In a positive resist, a high-molecular-weight polymer obtained by introducing a protecting group, which is decomposed by the action of an acid, into the resist base resin is used. Examples of the protecting group include tertiary alkyl groups, trialkylsilyl groups, oxoalkyl groups, aryl group-substituted alkyl groups, heteroalicyclic groups such as a tetrahydropyran-2-yl group, tertiary alkylcarbonyl groups, tertiary alkylcarbonylalkyl groups, tertiary alkyloxycarbonyl groups, tertiary alkyloxycarbonylalkyl groups, alkoxyalkyl groups, and acetal groups such as a tetrahydropyranyl group, a tetrahydrofuranyl group and a thiofuranyl group.

In a negative resist, a resin obtained by a reaction between the resist base resin and a cross-linking agent is used. The cross-linking agent can be arbitrarily selected from those resins that are commonly used as cross-linking agents, and examples thereof include amino resins having a hydroxyl group or an alkoxyl group, such as melamine resins, urea resins, guanamine resins, glycoluril-formaldehyde resins, succinylamide-formaldehyde resins and ethylene urea-formaldehyde resins. As these cross-linking agents, melamine, urea, guanamine, glycoluril, succinylamide and ethylene urea that are each methylolated through reaction with formalin in boiling water, or the resultants thereof further alkoxylated through reaction with a lower alcohol, can be used.

As the cross-linking agent, a commercially available one can be used as well, and examples thereof include NIKALAC MX-750, NIKALAC MW-30, and NIKALAC MX-290 (manufactured by Sanwa Chemical Co., Ltd.).

When the aromatic sulfonium salt compound of the present invention is used as a photoacid generator, other photoacid generator such as an iodonium salt compound or a sulfonium compound may also be used in combination. When other photoacid generator is used, it is preferably used in an amount of 10 to 200 parts by mass with respect to 100 parts by mass of the aromatic sulfonium salt compound of the present invention.

In the resist composition of the present invention, in addition to a photoacid generator other than the aromatic sulfonium salt compound of the present invention, a variety of resin additives, such as an unsaturated bond-containing monomer, a chain transfer agent, a surfactant, a thermoplastic organic polymer, a thermal polymerization inhibitor, a base quencher, an acid amplifier, an acid dispersant, a base generator, an inorganic filler, an organic filler, a coloring agent (e.g., pigment or dye), an antifoaming agent, a thickening agent, a flame retardant, a UV absorber, an antioxidant, a stabilizer, a sensitizer, a plasticizer, an adhesion promoter, an antistatic agent, a lubricant, a crystallizer, a dispersant, a leveling agent and a silane-coupling agent, can be incorporated. In the resist composition of the present invention, these additives are used in a total amount of preferably 50% by mass or less.

Prior to its use, the resist composition of the present invention is normally adjusted by being dissolved in a solvent to a total solid concentration of usually 5 to 50% by weight, preferably 10 to 25% by weight, and subsequently filtered through, for example, a filter having a pore size of about 0.2 μm. The resist composition of the present invention can be prepared by a method of, for example, mixing, dissolving or kneading a photoacid generator composed of the aromatic sulfonium salt compound of the present invention, other photoacid generator(s), a resist base resin and other arbitrary component(s).

A light source used for the exposure of the resist composition of the present invention is selected as appropriate from those emitting g-line (436 nm), h-line (405 nm), i-line (365 nm), visible light, ultraviolet radiation, far-ultraviolet radiation, X-ray, charged particle beam or the like in accordance with the type of the photoacid generator(s) in use, and the aromatic sulfonium salt compound of the present invention can be suitably applied to a resist which utilizes g-line (436 nm), h-line (405 nm), i-line (365 nm), visible light or the like.

The resist composition of the present invention is coated on a substrate made of silicon or the like by an appropriate coating method using a spinner, a coater or the like, subsequently exposed through a prescribed mask, post-baked for improvement of the apparent sensitivity of the resulting resist and then developed, whereby a more favorable resist pattern can be obtained.

Next, the cationic polymerization initiator of the present invention will be described.

The cationic polymerization initiator of the present invention comprises the aromatic sulfonium salt compound of the present invention. The amount thereof to be used is not particularly restricted; however, it is preferably 0.01 to 100 parts by mass, more preferably 0.05 to 20 parts by mass, with respect to 100 parts by mass of a cationically polymerizable compound. In this case, when the cationic polymerization initiator is used in an amount of less than 0.01 parts by mass, the sensitivity may be reduced, whereas when the amount is greater than 20 parts by mass, the transparency to radiation may be deteriorated. It is noted here, however, that the cationic polymerization initiator of the present invention may be used in an amount that is greater or less than the above-described range, depending on the factors such as the properties of the cationically polymerizable compound, the light irradiation intensity, the time required for reaction, the physical properties and the cost.

Next, the cationically polymerizable composition of the present invention will be described.

The cationically polymerizable composition of the present invention is a composition which comprises the cationic polymerization initiator of the present invention and a cationically polymerizable compound. The term "cationically polymerizable compound" used herein means a compound whose polymerization or cross-linking reaction is induced by a cationic polymerization initiator activated by irradiation with light, and such a compound is used individually, or in combination of two or more thereof.

Examples of the cationically polymerizable compound include epoxy compounds, oxetane compounds, cyclic lactone compounds, cyclic acetal compounds, cyclic thioether compounds, spiro-orthoester compounds and vinyl compounds, and one or more of these compounds can be used. Thereamong, epoxy compounds and oxetane compounds are suitable because of their availability and ease of handling. Particularly, as the epoxy compounds, for example, alicyclic epoxy compounds, aromatic epoxy compounds and aliphatic epoxy compounds are suitable.

Examples of the alicyclic epoxy compounds include polyglycidyl ethers of polyhydric alcohols having at least one alicyclic ring; and cyclohexene oxide or cyclopentene oxide-containing compounds obtained by epoxidation of cyclohexene or a cyclopentene ring-containing compound with an oxidizing agent. Examples of these compounds include hydrogenated bisphenol-A diglycidyl ether, 3,4-epoxycyclohexylmethyl-3,4-epoxycyclohexane carboxylate, 3,4-epoxy-1-methylcyclohexyl-3,4-epoxy-1-methylcyclohexane carboxylate, 6-methyl-3,4-epoxycyclohexylmethyl-6-methyl-3,4-epoxycyclohexane carboxylate, 3,4-epoxy-3-methylcyclohexylmethyl-3,4-epoxy-3-methylcyclohexane carboxylate, 3,4-epoxy-5-methylcyclohexylmethyl-3,4-epoxy-5-methylcyclohexane carboxylate, 2-(3,4-epoxycyclohexyl-5,5-spiro-3,4-epoxy)cyclohexane-metadioxane, bis(3,4-epoxycyclohexylmethyl) adipate, 3,4-epoxy-6-methylcyclohexyl carboxylate, methylene-bis(3,4-epoxycyclohexane), dicyclopentadiene diepoxide, ethylene-bis(3,4-epoxycyclohexanecarboxylate), dioctyl epoxyhexahydrophthalate, and di-2-ethylhexyl epoxyhexahydrophthalate.

Examples of commercially available products that can be suitably used as an alicyclic epoxy compound include UVR-6100, UVR-6105, UVR-6110, UVR-6128 and UVR-6200 (all of which are manufactured by Union Carbide Corporation); CELLOXIDE 2021, CELLOXIDE 2021P, CELLOXIDE 2081, CELLOXIDE 2083, CELLOXIDE 2085, CELLOXIDE 2000, CELLOXIDE 3000, CYCLOMER A200, CYCLOMER M100, CYCLOMER M101, EPOLEAD GT-301, EPOLEAD GT-302, EPOLEAD 401, EPOLEAD 403, ETHB and EPOLEAD HD300 (all of which are manufactured by Daicel Chemical Industries, Ltd.); and KRM-2110 and KRM-2199 (both of which are manufactured by ADEKA Corporation).

Among these alicyclic epoxy compounds, epoxy resins having a cyclohexene oxide structure are preferred because of their curability (curing rate).

Further, specific examples of the aromatic epoxy compounds include polyglycidyl ethers of polyhydric phenols having at least one aromatic ring or alkylene oxide adducts thereof, such as glycidyl ethers of bisphenol A, bisphenol F or an alkylene oxide adduct thereof; and epoxy novolac resins.

Specific examples of the aliphatic epoxy compounds include polyglycidyl ethers of aliphatic polyhydric alcohols or alkylene oxide adducts thereof; polyglycidyl esters of aliphatic long-chain polybasic acids; homopolymers synthesized by vinyl polymerization of glycidyl acrylate or glycidyl methacrylate; and copolymers synthesized by vinyl polymerization of glycidyl acrylate or glycidyl methacrylate and other vinyl monomer(s). Representative examples of these compounds include glycidyl ethers of polyhydric alcohols, such as 1,4-butanediol diglycidyl ether, 1,6-hexanediol diglycidyl ether, glycerol triglycidyl ether, trimethylolpropane triglycidyl ether, sorbitol tetraglycidyl ether, dipentaerythritol hexaglycidyl ether, polyethylene glycol diglycidyl ether and polypropylene glycol diglycidyl ether; polyglycidyl ethers of polyether polyols obtained by addition of one or more alkylene oxides to an aliphatic polyhydric alcohol, such as propylene glycol, trimethylolpropane and glycerin; and diglycidyl esters of aliphatic long-chain dibasic acids. Examples thereof also include monoglycidyl ethers of aliphatic higher alcohols; monoglycidyl ethers of phenol, cresol, butylphenol, or polyether alcohols obtained by addition of an alkylene oxide thereto; glycidyl esters of higher fatty acids; epoxidized soybean oil; octyl epoxystearate; butyl epoxystearate; and epoxidized polybutadienes.

Examples of commercially available products that can be suitably used as an aromatic compound or an aliphatic epoxy compound include EPIKOTE 801 (jER801) and EPIKOTE 828 (jER828) (both of which are manufactured by Mitsubishi Chemical Corporation); PY-306, 0163, and DY-022 (all of which are manufactured by BASF Japan, Ltd.); KRM-2720, EP-4100, EP-4000, EP-4080, EP-4900, ED-505 and ED-506 (all of which are manufactured by ADEKA Corporation); EPOLIGHT M-1230, EPOLIGHT EHDG-L, EPOLIGHT 40E, EPOLIGHT 100E, EPOLIGHT 200E, EPOLIGHT 400E, EPOLIGHT 70P, EPOLIGHT 200P, EPOLIGHT 400P, EPOLIGHT 1500NP, EPOLIGHT 1600, EPOLIGHT 80MF, EPOLIGHT 100MF, EPOLIGHT 4000, EPOLIGHT 3002 and EPOLIGHT FR-1500 (all of which are manufactured by Kyoeisha Chemical Co., Ltd.); and SUNTOHTO ST0000, YD-716, YH-300, PG-202, PG-207, YD-172 and YDPN638 (all of which are manufactured by Tohto Kasei Co., Ltd.).

Further, specific examples of the oxetane compounds include the following compounds: 3-ethyl-3-hydroxymethyloxetane, 3-(meth)allyloxymethyl-3-ethyloxetane, (3-ethyl-3-oxetanylmethoxy)methylbenzene, 4-fluoro-[1-(3-ethyl-3-oxetanylmethoxy)methyl]benzene, 4-methoxy-[1-(3-ethyl-3-oxetanylmethoxy)methyl]benzene, [1-(3-ethyl-3-oxetanylmethoxy)ethyl]phenyl ether, isobutoxymethyl(3-ethyl-3-oxetanylmethyl)ether, isobornyloxyethyl(3-ethyl-3-oxetanylmethyl)ether, isobornyl(3-ethyl-3-oxetanylmethyl)ether, 2-ethylhexyl(3-ethyl-3-oxetanylmethyl)ether, ethyldiethylene glycol (3-ethyl-3-oxetanylmethyl)ether, dicyclopentadiene(3-ethyl-3-oxetanylmethyl)ether, dicyclopentenyloxyethyl(3-ethyl-3-oxetanylmethyl)ether, dicyclopentenyl(3-ethyl-3-oxetanylmethyl)ether, tetrahydrofurfuryl(3-ethyl-3-oxetanylmethyl)ether, tetrabromophenyl(3-ethyl-3-oxetanylmethyl)ether, 2-tetrabromophenoxyethyl(3-ethyl-3-oxetanylmethyl)ether, tribromophenyl(3-ethyl-3-oxetanylmethyl)ether, 2-tribromophenoxyethyl(3-ethyl-3-oxetanylmethyl)ether, 2-hydroxyethyl(3-ethyl-3-oxetanylmethyl)ether, 2-hydroxypropyl(3-ethyl-3-oxetanylmethyl)ether, butoxyethyl(3-ethyl-3-oxetanylmethyl)ether, pentachlorophenyl(3-ethyl-3-oxetanylmethyl)ether, pentabromophenyl(3-ethyl-3-oxetanylmethyl)ether, bornyl(3-ethyl-3-oxetanylmethyl) ether, 3,7-bis(3-oxetanyl)-5-oxa-nonane, 3,3'-(1,3-(2-methylenyl)propanediyl-bis(oxymethylene))bis-(3-ethyloxetane), 1,4-bis[(3-ethyl-3-oxetanylmethoxy)methyl]benzene, 1,2-bis[(3-ethyl-3-oxetanylmethoxy)methyl]ethane, 1,3-bis[(3-ethyl-3-oxetanylmethoxy)methyl]propane, ethylene glycol-bis(3-ethyl-3-oxetanylmethyl)ether, dicyclopentenyl-bis(3-ethyl-3-oxetanylmethyl)ether, triethylene glycol-bis(3-ethyl-3-oxetanylmethyl)ether, tetraethylene glycol-bis(3-ethyl-3-oxetanylmethyl)ether, tricyclodecane-diyldimethylene(3-ethyl-3-oxetanylmethyl)ether, trimethylolpropane tris(3-ethyl-3-oxetanylmethyl)ether, 1,4-bis(3-ethyl-3-oxetanylmethoxy)butane, 1,6-bis(3-ethyl-3-oxetanylmethoxy)hexane, pentaerythritol tris(3-ethyl-3-oxetanylmethyl)ether, pentaerythritol tetrakis(3-ethyl-3-oxetanylmethyl)ether, polyethylene glycol-bis(3-ethyl-3-oxetanylmethyl)ether, dipentaerythritol hexakis(3-ethyl-3-oxetanylmethyl)ether, dipentaerythritol pentakis(3-ethyl-3-oxetanylmethyl)ether, dipentaerythritol tetrakis(3-ethyl-3-oxetanylmethyl)ether, caprolactone-modified dipentaerythritol hexakis(3-ethyl-3-oxetanylmethyl)ether, caprolactone-modified dipentaerythritol pentakis(3-ethyl-3-oxetanylmethyl)ether, ditrimethylolpropane tetrakis(3-ethyl-3-oxetanylmethyl)ether, EO-modified bisphenol A-bis(3-ethyl-3-oxetanylmethyl)ether, PO-modified bisphenol A-bis(3-ethyl-3-oxetanylmethyl)ether, EO-modified hydrogenated bisphenol A-bis(3-ethyl-3-oxetanylmethyl)ether, PO-modified hydrogenated bisphenol A-bis(3-ethyl-3-oxetanylmethyl)ether, and EO-modified bisphenol F-(3-ethyl-3-oxetanylmethyl)ether.

The use of these oxetane compounds is effective and thus preferred particularly when flexibility is required.

Specific examples of other compounds used as the cationically polymerizable compound include cyclic lactone compounds, such as fl-propiolactone and ε-caprolactone; cyclic acetal compounds, such as trioxane, 1,3-dioxolane and 1,3,6-trioxanecyclooctane; cyclic thioether compounds, such as tetrahydrothiophene derivatives; spiro-orthoester compounds obtained by reaction between any of the above-described epoxy compounds and lactone; vinyl ether compounds, such as ethylene glycol divinyl ether, alkyl vinyl ether, 2-chloroethyl vinyl ether, 2-hydroxyethyl vinyl ether, triethylene glycol divinyl ether, 1,4-cyclohexanedimethanol divinyl ether, hydroxybutyl vinyl ether, and the propenyl ether of propylene glycol; vinyl compounds, such as ethylenically unsaturated compounds, including styrene, vinylcyclohexene, isobutylene and polybutadiene; oxolane compounds, such as tetrahydrofuran and 2,3-dimethyltetrahydrofuran; thiirane compounds, such as ethylene sulfide and thioepichlorohydrin; thietane compounds, such as 1,3-propyne sulfide and 3,3-dimethylthietane; and silicones, all of which compounds are well-known.

Further, in order to facilitate dissolution of the aromatic sulfonium salt compound of the present invention into the cationically polymerizable compound, the aromatic sulfonium salt compound of the present invention, prior to its use, can be dissolved in an appropriate solvent in advance (e.g., propylene carbonate, carbitol, carbitol acetate, butyrolactone or propylene glycol-1-monomethyl ether-2-acetate).

By irradiating the cationically polymerizable composition of the present invention with an energy beam such as ultraviolet radiation, the cationically polymerizable composition can be cured to a dry-to-touch state or solvent-insoluble state in usually 0.1 seconds to several minutes thereafter. As an appropriate energy beam, any energy beam may be used as long as it induces decomposition of the cationic polymerization initiator; however, it is preferred to use an electromagnetic energy beam having a wavelength of 2,000 Å to 7,000 Å that is emitted from, for example, an ultrahigh, high, medium or low-pressure mercury lamp, a xenon lamp, a carbon arc lamp, a metal halide lamp, a fluorescent lamp, a tungsten lamp, an excimer lamp, a germicidal lamp, an excimer laser, a nitrogen laser, an argon ion laser, a helium-cadmium laser, a helium neon laser, a krypton ion laser, a semiconductor laser, a YAG laser, a light-emitting diode or a CRT light source; or a high-energy beam such as an electron beam, X-ray or radiation.

The time of exposure to the energy beam is variable depending on the intensity of the energy beam, the coating film thickness and the cationically polymerizable organic compound; however, an exposure of 0.1 seconds to about 10 seconds is usually sufficient. Still, a longer irradiation time is preferred for a relatively thick coating material. By the time of 0.1 seconds to several minutes after the energy beam irradiation, the composition is mostly in a dry-to-touch state as a result of cationic polymerization; however, depending on the case, it is also preferred to use thermal energy provided by heating, a thermal head or the like in combination so as to accelerate the cationic polymerization.

Specific examples of the application of the resist composition and cationically polymerizable composition of the present invention include, but not particularly limited to: optical filters; paints; coating agents; lining agents; adhesives; printing plates; insulating varnishes; insulation sheets; laminated plates; printed circuit boards; sealants for semiconductor devices, LED packages, liquid crystal inlets, organic EL devices, optical elements, electrical insulating materials, electronic components, separation membranes and the like; molded materials; putties; glass fiber impregnants; fillers; passivation films for semiconductors, solar cells and the like; interlayer insulation films and surface protection films that are used in thin-film transistors (TFT), liquid crystal displays, organic EL displays, printed boards and the like; color filters of printed boards, color televisions, PC monitors, personal digital assistants and CCD image sensors; electrode materials for plasma display panels; printing inks; dental compositions; resins for stereolithography; liquid-form films and dry films; micromachine components; glass fiber cable coatings; materials for holographic recording; magnetic recording materials; optical switches; plating masks; etching masks; screen printing stencils; touch panels such as transparent conductive films; MEMS elements; nanoimprint materials; photofabrication applications such as two-dimensional and three-dimensional high-density mounting and the like of semiconductor packages; decoration sheets; artificial nails; glass-alternative optical films; electronic papers; optical disks; micro-lens arrays used in projectors, optical communication lasers and the like; prism lens sheets used in backlights of liquid crystal displays; Fresnel lens sheets used in the screens of projection televisions and the like; lens parts of lens sheets such as lenticular lens sheets; backlights and the like using such sheets; optical lenses such as microlenses and image pickup lenses; optical elements; optical connectors; optical waveguides; insulation packings; heat-shrinkable rubber tubes; O-rings; sealing agents for display devices; protective materials; optical fiber protection materials; adhesives; die bonding agents; high-heat radiation materials; high-heat-resistant sealing materials; members for solar cells, fuel cells and secondary batteries; solid electrolytes for batteries; insulation coating materials; heat-sensitive drums for copying machines; gas separation membranes; civil engineering and construction materials, such as concrete protecting materials, linings, soil injection agents, sealing agents, cold-heat storage materials, glass coatings and foams; medical materials such as tube/seal materials, coating materials, sealing materials for sterilizers, contact lenses, oxygen enrichment membranes and biochips; automobile components; and various mechanical components.

EXAMPLES

The present invention will now be described in more detail by way of examples thereof; however, the present invention is not restricted by the following examples and the like by any means.

Examples 1-1 to 1-4 and Comparative Examples 1-1 to 1-3

<Preparation Example of Negative Resist Composition>

A resin solution was prepared by dissolving 100 g of EPPN-201 (manufactured by Nippon Kayaku Co., Ltd.) in 100 g of methyl ethyl ketone and, in 8.0 g of this resin solution, Compound Nos. 1, 2, 8 and 9 and the below-described Comparative Compound Nos. 1 to 3 were each dissolved in an amount of 0.05 g, whereby negative resist compositions of Examples 1-1 to 1-4 and Comparative Examples 1-1 to 1-3 were prepared, respectively.

Comparative Compound No. 1

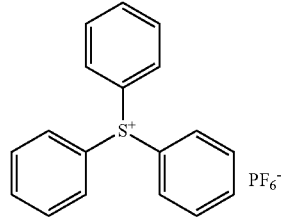

Comparative Compound No. 2

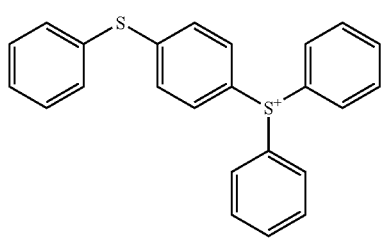

Comparative Compound No. 3

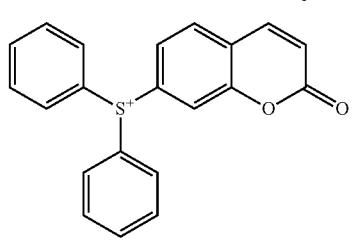

The thus obtained negative resist compositions were each coated on a piece of aluminum-coated paper using a #3 bar coater and subsequently irradiated with the light of an 80-W/cm high-pressure mercury lamp using a belt conveyor-equipped irradiation apparatus. The distance between the lamp and the belt conveyor was set at 10 cm, and the line speed of the belt conveyor was set at 8 m/min. The coated compositions were each allowed to cure and then left to stand at room temperature for 24 hours. The resulting coating films were not damaged even when they were rubbed back and forth 200 times with a cotton swab soaked in methyl ethyl ketone; therefore, it was confirmed that the curing progressed sufficiently.

<Evaluation of Hammett Acidity Function ($H_0$)>

For each of Compound Nos. 1, 2, 8 and 9 and Comparative Compound Nos. 1 to 3, the Hammett acidity function ($H_0$) of the acid species generated therefrom after photodegradation was measured in accordance with the method described in "Advances in Catalysis" (volume 37, pp. 186-187). The results thereof are shown in Table 1.

TABLE 1

|  | Compound | $H_0$ |
| --- | --- | --- |
| Example 1-1 | Compound No. 1 | +0.55 |
| Example 1-2 | Compound No. 2 | −13.2 |
| Example 1-3 | Compound No. 8 | +0.55 |
| Example 1-4 | Compound No. 9 | −13.2 |
| Comparative Example 1-1 | Comparative Compound No. 1 | −20 |
| Comparative Example 1-2 | Comparative Compound No. 2 | −20 |
| Comparative Example 1-3 | Comparative Compound No. 3 | −20 |

Examples 2-1 to 2-4 and Comparative Examples 2-1 to 2-3

<Preparation Example of Cationically Polymerizable Composition>

To a mixture of 80 g of 3,4-epoxycyclohexylmethyl-3,4-epoxycyclohexyl carboxylate and 20 g of 1,4-butanediol diglycidyl ether, Compound Nos. 1, 2, 8 and 9 and Comparative Compound Nos. 1 to 3 were each added in an amount of 4 mmol, and the resultants were thoroughly stirred to homogeneity, whereby cationically polymerizable compositions of Examples 2-1 to 2-4 and Comparative Examples 2-1 to 2-3 were prepared, respectively.

The thus obtained cationically polymerizable compositions were each coated on a piece of aluminum-coated paper using a #3 bar coater and subsequently irradiated with the light of an 80-W/cm high-pressure mercury lamp using a belt conveyor-equipped irradiation apparatus. The distance between the lamp and the belt conveyor was set at 10 cm, and the line speed of the belt conveyor was set at 8 m/min. The coated compositions were each allowed to cure and then left to stand at room temperature for 24 hours. The resulting coating films were not damaged even when they were rubbed back and forth 200 times with a cotton swab soaked in methyl ethyl ketone; therefore, it was confirmed that the curing progressed sufficiently.

<Evaluation of Acid Generation Rate>

For each of Compound Nos. 1, 2, 8 and 9 and Comparative Compound Nos. 1 to 3, a 0.5%-by-mass acetonitrile/water mixed solution (volume ratio: acetonitrile/water=9/1) was prepared, and 5.0 g thereof was placed in a Petri dish having an inner diameter of 50 mm. Using a UV lamp and a cut filter transmitting only light having a wavelength of about 365 nm (manufactured by Hoya Candeo Optronics Corporation), the mixed solution was irradiated with UV having an intensity of 100 mW/cm$^2$. The irradiation was performed for 2 seconds, 5 seconds and 10 seconds for each solution. After this exposure, the resultant was diluted with 45 g of acetonitrile/water mixed solution (volume ratio: acetonitrile/water=9/1) and subsequently titrated with a 0.1 mol/L aqueous potassium hydroxide solution using an automatic titrator manufactured by Hiranuma Sangyo Co., Ltd. (COM-1600). The acid concentration was determined based on the volume of the aqueous solution used, and the acid generation rate (mol %) was calculated therefrom. The results thereof are shown in Table 2.

TABLE 2

|  | Compound | Acid generation rate with 2-second irradiation (mol %) | Acid generation rate with 5-second irradiation (mol %) | Acid generation rate with 10-second irradiation (mol %) |
| --- | --- | --- | --- | --- |
| Example 2-1 | Compound No. 1 | 37.6 | 78.6 | 96.7 |
| Example 2-2 | Compound No. 2 | 38.7 | 80.9 | 96.8 |
| Example 2-3 | Compound No. 8 | 37.5 | 77.7 | 98.9 |
| Example 2-4 | Compound No. 9 | 35.0 | 78.5 | 98.7 |
| Comparative Example 2-1 | Comparative Compound No. 1 | 0 | 0 | 0 |
| Comparative Example 2-2 | Comparative Compound No. 2 | 13.8 | 27.6 | 45.9 |
| Comparative Example 2-3 | Comparative Compound No. 3 | —*1 | —*1 | —*2 |

*1 could not be evaluated since the film was not cured due to low acid generation rate
*2 not evaluated Examples 3-1 to 3-4 and Comparative Examples 3-1 to 3-3

A resin solution was prepared by dissolving 100 g of EPPN-201 (manufactured by Nippon Kayaku Co., Ltd.) in 100 g of methyl ethyl ketone (MEK) and, in 8.00 g of this resin solution, Compound Nos. 1, 2, 8 and 9 and Comparative Compound Nos. 1 to 3 were each dissolved in an amount of 0.05 g, whereby resist solutions were prepared. The thus obtained resist solutions were each coated on a copper substrate using a spin coater, dried at 90° C. for 90 seconds, and then irradiated with a light having a wavelength of 365 nm for exposure. The resultants were each baked at 110° C. for 90 seconds, developed by 30-second immersion in a 2.38% aqueous tetramethylammonium hydroxide solution, and then washed with pure water.

<Evaluation of Substrate Corrosion after Development>

For each of the thus washed copper substrates, the surface roughness (surface roughness of photosensitive resin composition layer; Ra, unit=nm) was measured under an atomic force microscope (AFM). A smaller value thereof means a smoother surface. The evaluation was made based on the following criteria. The results thereof are shown in Table 3.

○: Ra=2.0 nm to no more than 7.0 nm (range for practical use)
x: Ra=7.0 nm or not less (not practically usable)
-: not evaluated

TABLE 3

|  | Compound | Surface roughness |
| --- | --- | --- |
| Example 3-1 | Compound No. 1 | ○ |
| Example 3-2 | Compound No. 2 | ○ |
| Example 3-3 | Compound No. 8 | ○ |
| Example 3-4 | Compound No. 9 | ○ |
| Comparative Example 3-1 | Comparative Compound No. 1 | — |
| Comparative Example 3-2 | Comparative Compound No. 2 | x |
| Comparative Example 3-3 | Comparative Compound No. 3 | — |

From the results shown in Table 1, it is seen that the aromatic sulfonium salt compounds represented by the Formula (I) generated an acid species having a Hammett acidity function ($H_0$) of not less than −17 after being photodegrade, and that the strength of the generated acid was weaker than that of the acid generated by Comparative Compounds.

Further, from the results shown in Table 2, it is seen that the aromatic sulfonium salt compounds according to the present invention had a high acid generation capacity.

Moreover, from the results shown in Table 3, it is seen that the films obtained from the negative resist compositions comprising the aromatic sulfonium salt compounds according to the present invention exhibited low corrosion to the substrate after the development.

From the above, in the aromatic sulfonium salt compound of the present invention, since the organic anion generates a weak acid (an organic sulfonic acid having a Hammett acidity function ($H_0$) of not less than −17), the aromatic sulfonium salt compound of the present invention is less corrosive to a substrate than Comparative Examples and sufficiently generates such an acid; therefore, the aromatic sulfonium salt compound of the present invention has excellent photolithographic characteristics and can thus be suitably used as a photoacid generator in a resist composition for photolithography.

The invention claimed is:

1. An aromatic sulfonium salt compound of the following Formula (I):

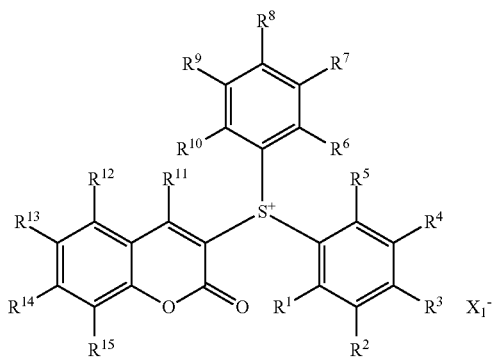

(I)

wherein,
$R^1$ to $R^{10}$ each independently represent a hydrogen atom, a halogen atom, a hydroxyl group, a nitro group, a cyano group, an alkyl group having 1 to 18 carbon atoms which is optionally substituted, an aryl group having 6 to 20 carbon atoms which is optionally substituted, or an arylalkyl group having 7 to 20 carbon atoms which is optionally substituted;

methylene chains in said alkyl group having 1 to 18 carbon atoms, said aryl group having 6 to 20 carbon atoms and said arylalkyl group having 7 to 20 carbon atoms, which groups are represented by $R^1$ to $R^{10}$, are optionally interrupted by —O—, —S—, —CO—, —CO—O— or —O—CO—;

$R^{11}$ to $R^{15}$ each independently represent a hydrogen atom, an alkoxy group having 1 to 18 carbon atoms which is optionally substituted, an arylalkoxy group having 7 to 20 carbon atoms which is optionally substituted, a thioalkyl group having 1 to 18 carbon atoms which is optionally substituted, an arylthioalkyl group having 7 to 20 carbon atoms which is optionally substituted, or —NRR';

R and R' each independently represent a hydrogen atom, an alkyl group having 1 to 10 carbon atoms, or an aryl group having 6 to 12 carbon atoms;

at least one of $R^{11}$ to $R^{15}$ is not a hydrogen atom; and $X_1^-$ represents a monovalent organic sulfonate anion.

2. An aromatic sulfonium salt compound of the following Formula (II):

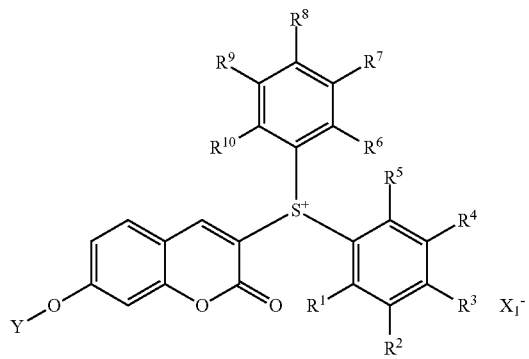

(II)

wherein,
$R^1$ to $R^{10}$ each independently represent a hydrogen atom, a halogen atom, a hydroxyl group, a nitro group, a cyano group, an alkyl group having 1 to 18 carbon atoms which is optionally substituted, an aryl group having 6 to 20 carbon atoms which is optionally substituted, or an arylalkyl group having 7 to 20 carbon atoms which is optionally substituted;

methylene chains in said alkyl group having 1 to 18 carbon atoms, said aryl group having 6 to 20 carbon atoms and said arylalkyl group having 7 to 20 carbon atoms, which groups are represented by $R^1$ to $R^{10}$, are optionally interrupted by —O—, —S—, —CO—, —CO—O— or —O—CO—;

$X_1^-$ represents a monovalent organic sulfonate anion; and

Y represents an alkyl group having 1 to 18 carbon atoms or an arylalkyl group having 7 to 20 carbon atoms.

3. A photoacid generator, comprising the aromatic sulfonium salt compound according to claim 1.

4. A resist composition, comprising the photoacid generator according to claim 3.

5. The resist composition according to claim 4, which is a positive or negative resist composition for i-line.

6. A cationic polymerization initiator, comprising the aromatic sulfonium salt compound according to claim 1.

7. A cationically polymerizable composition, comprising the cationic polymerization initiator according to claim 6.

8. A photoacid generator, comprising the aromatic sulfonium salt compound according to claim 2.

9. A cationic polymerization initiator, comprising the aromatic sulfonium salt compound according to claim 2.

* * * * *